US009206442B2

(12) United States Patent
Chen

(10) Patent No.: US 9,206,442 B2
(45) Date of Patent: Dec. 8, 2015

(54) METHOD FOR ENZYMATIC TREATMENT OF TISSUE PRODUCTS

(75) Inventor: Yi Chen, Lawrenceville, NJ (US)

(73) Assignee: LifeCell Corporation, Branchburg, NJ (US)

( * ) Notice: Subject to any disclaimer, the term of this patent is extended or adjusted under 35 U.S.C. 154(b) by 510 days.

(21) Appl. No.: 13/457,791

(22) Filed: Apr. 27, 2012

(65) Prior Publication Data

US 2012/0276213 A1    Nov. 1, 2012

Related U.S. Application Data

(60) Provisional application No. 61/479,937, filed on Apr. 28, 2011.

(51) Int. Cl.
| | |
|---|---|
| *C12P 1/00* | (2006.01) |
| *A61K 35/12* | (2015.01) |
| *A61L 27/56* | (2006.01) |
| *A61L 27/36* | (2006.01) |

(52) U.S. Cl.
CPC .............. *C12P 1/00* (2013.01); *A61L 27/3604* (2013.01); *A61L 27/3662* (2013.01); *A61L 27/3687* (2013.01); *A61L 27/56* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 5,336,616 A | 8/1994 | Livesey et al. | |
| 5,364,756 A | 11/1994 | Livesey et al. | |
| 6,166,288 A | 12/2000 | Diamond et al. | |
| 6,381,026 B1 | 4/2002 | Schiff et al. | |
| 6,933,326 B1 | 8/2005 | Griffey et al. | |
| 7,358,284 B2 | 4/2008 | Griffey et al. | |
| 2003/0035843 A1 | 2/2003 | Livesey et al. | |
| 2003/0143207 A1 | 7/2003 | Livesey et al. | |
| 2005/0028228 A1 | 2/2005 | McQuillan et al. | |
| 2006/0073592 A1 | 4/2006 | Sun et al. | |
| 2006/0127375 A1 | 6/2006 | Livesey et al. | |
| 2006/0210960 A1 | 9/2006 | Livesey et al. | |
| 2007/0009586 A1 | 1/2007 | Cohen et al. | |
| 2007/0248575 A1 | 10/2007 | Connor et al. | |
| 2008/0027562 A1 | 1/2008 | Fujisato et al. | |
| 2009/0130221 A1 | 5/2009 | Bolland et al. | |
| 2009/0306790 A1 | 12/2009 | Sun | |
| 2010/0233235 A1* | 9/2010 | Matheny et al. | 424/423 |
| 2011/0021753 A1 | 1/2011 | Huang | |
| 2012/0276213 A1 | 11/2012 | Chen | |

FOREIGN PATENT DOCUMENTS

| | | |
|---|---|---|
| CN | 1266716 A | 9/2000 |
| WO | 99/44533 A1 | 9/1999 |
| WO | WO 01/91671 | 12/2001 |
| WO | 03/097694 A1 | 11/2003 |
| WO | WO-2007/043513 A1 | 4/2007 |
| WO | 2008125850 A2 | 10/2008 |

OTHER PUBLICATIONS

Badylak et al., "Extracellular Matrix as a Biological Scaffold Material: Structure and Function," Acta Biomaterialia (2008), doi:10.1016/j.actbio.2008.09.013.
Collins et al., "Cardiac Xenografts Between Primate Species Provide Evidence for the Importance of the α-Galactosyl Determinant in Hyperacute Rejection," J. Immunol. 154:5500-5510 (1995).
Galili et al., "Interaction between human natural anti-alpha-galactosyl immunoglobulin G and bacteria of the human flora," Infect. Immun. 56:1730-1737 (1988).
Galili et al., "Interaction of the natural anti-Gal antibody with α-galactosyl epitopes: a major obstacle for xenotransplantation in humans," Immunology Today 14: 480-482 (1993).
Galili et al., "Man, apes, and Old World monkeys differ from other mammals in the expression of alpha-galactosyl epitopes on nucleated cells," J. Biol. Chem. 263:17755-17762 (1988).
Good et al., "Identification of Carbohydrate Structures That Bind Human Antiporcine Antibodies: Implications for Discordant Xenografting in Humans," Transplant Proc. 24: 559-562 (1992).
Hamadeh et al., "Human natural anti-Gal IgG regulates alternative complement pathway activation on bacterial surfaces," J. Clin. Invest. 89:1223-1235 (1992).
International Search Report and Written Opinion for PCT/US2012/035361 mailed Jun. 28, 2012, from the International Searching Authority of the European Patent Office.
Ionescu et al., "Effect of Papain and Bromelin on Muscle and Collagen Proteins in Beef Meat," The Annals of the University Dunarea de Jos of Galati. Fascicle VI, Food Technology, New Series, pp. 9-16, 2008.
Sandrin et al., "Anti-pig IgM antibodies in human serum react predominantly with Gal(alpha 1-3)Gal epitopes," Proc. Natl. Acad. Sci. USA 90: 11391-11395 (1993).
Xu, "A Porcine-Derived Acellular Dermal Scaffold that Supports Soft Tissue Regeneration: Removal of Terminal Galactose-α-(1,3)-Galactose and Retention of Matrix Structure," Tissue Engineering, vol. 15, 1-13 (2009).
Dobrin, P.B. et al. "Elastase, collagenase, and the biaxial elastic properties of dog carotid artery" *Am. J. Physiol. Heart Circ. Physiol.* 247:H124-H131 (1984).
International Patent Application No. PCT/US2009/046193: International Search Report and Written Opinion; Date of mailing: Jul. 30, 2010 (12 pages).
Karlinsky, J.B. et al. "In Vitro Effects of Elastase and Collagenase on Mechanical Properties of Hamster Lungs" *Chest* 69(2):275-276 (1976).
Lu, Q. et al. "Novel Porous Aortic Elastin and Collagen Scaffolds for Tissue Engineering" *Biomaterials* 25(22):5227-5237 (2004).
Reihsner, R. et al. "Biomechanical properties of elastase treated palmar aponeuroses" *Connective Tissue Research* 26:77-86 (1991).
Tedder, M.E. et al. "Stabilized Collagen Scaffolds for Heart Valve Tissue Engineering" *Tissue Engineering: Part A* 00(00):1-12 (2008).
Yuan, H. et al. "Effects of collagenase and elastase on the mechanical properties of lung tissue strips" *J. App. Physiol.* 89:3-14 (2000).

* cited by examiner

*Primary Examiner* — Chris R Tate
*Assistant Examiner* — Douglas F White
(74) *Attorney, Agent, or Firm* — McCarter & English, LLP; Matthew R. Van Eman

(57) ABSTRACT

Methods for treating tissue matrices and tissue matrices produced according to the methods are provided. The methods can include treating a tissue matrix with a proteolytic enzyme to produce a desired pliability of the tissue matrix.

12 Claims, 4 Drawing Sheets

METHOD FOR ENZYMATIC TREATMENT OF TISSUE PRODUCTS

This application claim priority under 35 U.S.C. §119 to U.S. Provisional Application No. 61/479,937, which was filed on Apr. 28, 2011.

The present disclosure relates to tissue matrices, and more particularly, to methods for controlling the pliability of tissue matrices by treating the matrices with proteolytic enzymes.

Various tissue-derived products are used to regenerate, repair, or otherwise treat diseased or damaged tissues and organs. Such products can include intact tissue grafts and/or acellular or reconstituted acellular tissues (e.g., acellular tissue matrices from skin, intestine, or other tissues, with or without cell seeding). Such products generally have mechanical properties determined by the tissue source (i.e., tissue type and animal from which it originated) and the processing parameters used to produce the tissue products. Since tissue products are often used for surgical applications and/or tissue replacement or augmentation, the mechanical properties of the tissue products are important. For example, surgeons generally prefer tissues that feel more natural and/or are easy to handle during surgical procedures. However, some tissue products are undesirably stiff and have an unnatural feel. Accordingly, methods for treating the tissue products to produce more desirable mechanical properties are provided.

SUMMARY

According to certain embodiments, a method for treating a tissue matrix is provided. The method can comprise selecting a collagen-containing tissue matrix and contacting the tissue matrix with a proteolytic enzyme under conditions sufficient to produce a desired level of pliability in the tissue matrix.

In another embodiment, a method for treating a tissue matrix is provided. The method can comprise selecting a collagen-containing acellular tissue matrix and contacting the tissue matrix with a proteolytic enzyme under conditions sufficient to produce a desired level of pliability in the tissue matrix and to increase the porosity of the tissue matrix.

In some embodiments, an acellular tissue matrix is provided. The matrix can be prepared by a processing comprising selecting an acellular tissue matrix and contacting the tissue matrix with a proteolytic enzyme under conditions sufficient to produce a desired level of pliability in the tissue matrix.

DESCRIPTION OF CERTAIN EXEMPLARY EMBODIMENTS

Figure 1A:
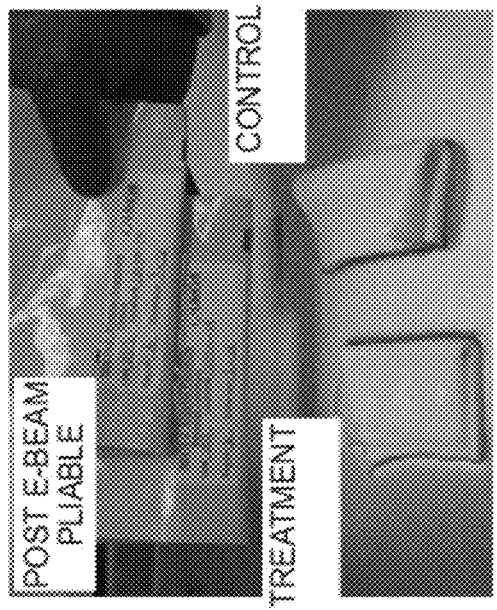
FIG. 1A-FIG. 1D show acellular tissue matrices after treatment with enzymes using methods of the present disclosure, as well as untreated controls.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" will refer to any human or animal tissue that contains an extracellular matrix proteins. "Tissue products" can include acellular or partially decellularized tissue matrices, decellularized tissue matrices that have been repopulated with exogenous cells, and/or cellular tissues that have been processed to change the orientation of at least some of the collagen fibers within the tissue's extracellular matrix.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

For surgical applications, it is often desirable to produce tissue products that have certain mechanical properties. For example, the tissue product, which may include a sheet of material, should possess sufficient strength to withstand the intended use. For example, certain tissue products may be used to repair defects (e.g., hernias), to support surrounding tissues or implants (e.g., for breast augmentation and/or reconstruction), or to replace damaged or lost tissue (e.g., after trauma or surgical resection). Whatever the particular use, the tissue product should have sufficient strength, elasticity, and/or other mechanical properties to function until tissue regeneration and/or repair occurs.

In addition, tissue products should have a desirable feel. For example, surgeons generally prefer materials that have a natural tissue-like feel (e.g., are sufficiently soft, pliable, and/or elastic). Further, after implantation it is desirable for tissue products to feel more natural. For example, tissues used for breast augmentation should not be excessively stiff so as to produce a more naturally feeling breast.

However, some tissue products can be excessively stiff. For example, some surgeons note that porcine-derived dermal materials such as STRATTICE™ are less pliable than human-dermal products such as ALLODERM®. However, processes for improving the feel of such products should not adversely affect the biological and/or mechanical properties of the products. Specifically, processing of the products to improve the feel of the products should not produce an undesirable decrease in other mechanical properties such as tensile strength, and should not alter the protein matrix in such a way that the material does not support tissue regeneration and/or repair.

The present disclosure provides methods for treating tissues to improve the feel of tissue products produced from the tissues. The disclosure also provides tissue products produced using the methods of treatments. In addition, the present disclosure provides methods of treating tissues to control the porosity of tissue products produced from the tissues. In some cases, controlling the porosity can improve cellular infiltration and tissue regeneration and/or repair.

Figure 1B:
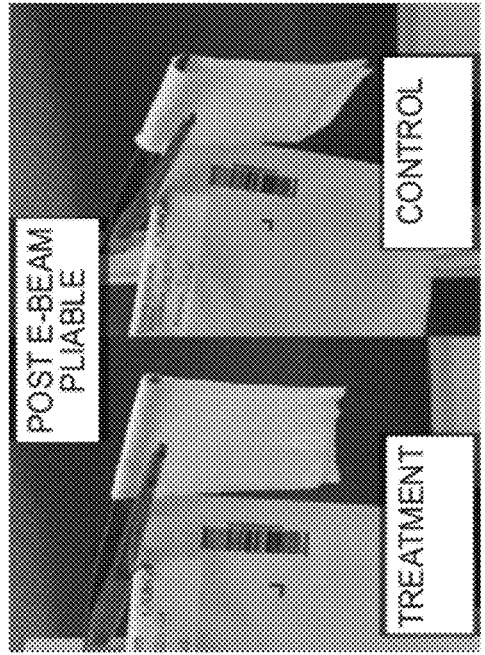
Figure 1C:
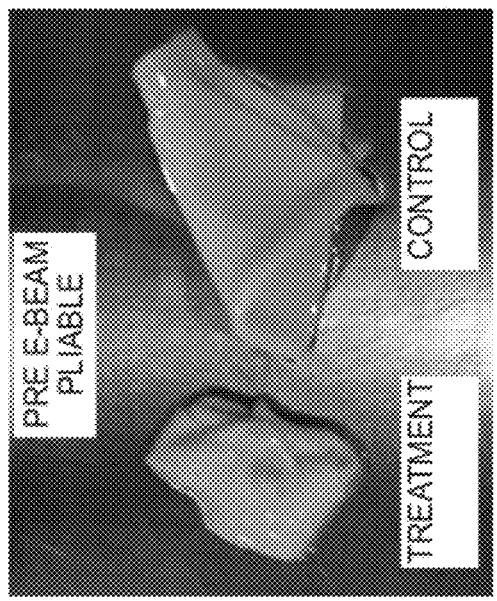
Figure 1D:
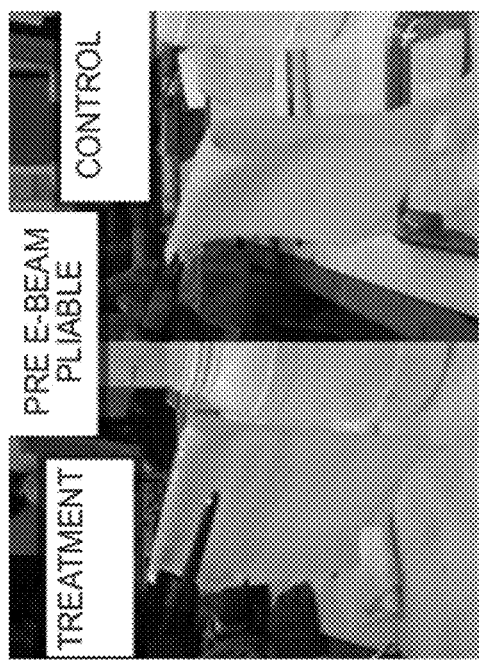

Accordingly, in one embodiment, a method for treating a tissue matrix is provided. The method can comprise selecting a collagen-containing tissue matrix and contacting the tissue matrix with a proteolytic enzyme under conditions sufficient to produce a desired level of pliability in the tissue matrix. In another embodiment, a method for treating a tissue matrix is provided. The method can comprise selecting a collagen-containing acellular tissue matrix and contacting the tissue matrix with a proteolytic enzyme under conditions sufficient to produce a desired level of pliability in the tissue matrix and to increase the porosity of the tissue matrix. FIG. 1A-FIG. 1D show acellular tissue matrices (STRATTICE™) after treatment with enzymes using methods of the present disclosure, as well as untreated controls. As shown, the treated samples are significantly more pliable.

In various embodiments, treatment of tissue matrices with proteolytic enzymes provides improved mechanical properties without causing degradation in one or biological properties. For example, treatment of tissue matrices can produce desired stiffness, feel, tactile properties, and/or desired porosity without causing increased inflammation or scar formation and/or without causing a reduction in the tissue matrices' ability to promote cell ingrowth and regeneration.

The tissues can be selected to provide a variety of different biological and mechanical properties. For example, an acellular tissue matrix or other tissue product can be selected to allow tissue in-growth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue product can be formed from ALLODERM® or STRATTICE™, which are human and porcine acellular dermal matrices respectively. Alternatively, other suitable acellular tissue matrices can be used, as described further below. The tissues can be selected from a variety of tissue sources including skin (dermis or whole skin), fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue. The methods described herein can be used to process any collagenous tissue type, and for any tissue matrix product. For example, a number of biological scaffold materials are described by Badylak et al., and the methods of the present disclosure can be used to treat those or other tissue products known in the art. Badylak et al., "Extracellular Matrix as a Biological Scaffold Material: Structure and Function," Acta Biomaterialia (2008), doi:10.1016/j.actbio.2008.09.013.

In some cases, the tissue matrix can be provided as a decellularized tissue matrix. Suitable acellular tissue matrices are described further below. In other cases, the method can further include processing intact tissue to remove cells or other materials. The tissues can be completely or partially decellularized to yield acellular tissue matrices or extracellular tissue materials to be used for patients. For example, various tissues, such as skin, intestine, bone, cartilage, nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous sources or other sources to facilitate treatment. Suitable processes for producing acellular tissue matrices are described below.

A number of different enzymes can be used to treat the tissue matrices. For example, suitable enzymes can include sulfhydryl proteases such as bromelain. In addition, they can include bromelain, papain, ficin, actinidin, or combinations thereof. The enzymes can be purchased commercially or extracted from fruit sources. For example, one source of bromelain is MCCORMICK MEAT TENDERIZER®, but the enzymes can also be extracted from pineapple and/or purchased in a medical-grade formulation.

The enzymes can be contacted with the tissues to increase the pliability of the tissue without causing undesirable degradation in other mechanical and/or biological properties. For example, when a batch of materials are produced with or without the enzyme treatments discussed herein, the enzyme treatments will not produce an undesirable change in at least one of tensile strength, tear strength, suture strength, creep resistance, collagenase susceptibility, glycosaminoglycan content, lectin content, burst strength, thermal transition temperature, or combinations thereof. In some cases, an undesirable change is a statistically significant reduction any one of tensile strength, tear strength, suture strength, creep resistance, glycosaminoglycan content, lectin content, burst strength; an increase in collagenase susceptibility; or a change (upward or downward) in thermal transition temperature (as measure using differential scanning calorimetry).

As noted above, in some embodiments, the tissues are treated with an enzyme to increase the porosity of the tissue. In various embodiments, increasing the porosity of the tissue is performed to increase the number and/or size of channels, which can improve the rate of cellular infiltration and tissue regeneration.

In some cases, the enzymes are selected such that they cause site-specific cleavage of proteins within the tissues. For example, it has been found that treatment of porcine dermal materials with bromelain does not cause further alterations in the matrix structure after a certain amount of treatment. Therefore, treatment of dermis with bromelain does not cause further change in the matrix with prolonged exposure or after extended periods of time.

In addition, the enzyme can be applied to the tissues in a variety of suitable solutions. For example, bromelain has been found to be effective when applied to tissues in normal saline, but other suitable buffers (e.g., PBS) can be used.

Acellular Tissue Matrices

The term "acellular tissue matrix," as used herein, refers generally to any tissue matrix that is substantially free of cells and/or cellular components. Skin, parts of skin (e.g., dermis), and other tissues such as blood vessels, heart valves, fascia, cartilage, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular. Skin, parts of skin (e.g., dermis), and other tissues such as blood vessels, heart valves, fascia, cartilage, bone, and nerve connective tissue may be used to create acellular matrices within the scope of the present disclosure.

In general, the steps involved in the production of an acellular tissue matrix include harvesting the tissue from a donor (e.g., a human cadaver or animal source) and cell removal under conditions that preserve biological and structural function. In one embodiment, the processing includes removing and discarding an epithelium (e.g., epidermis). In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

EXAMPLE

The following example illustrates a process for treating porcine dermal acellular tissue matrices with bromelain to increase the pliability of the material. As discussed below, the treatment did not cause an undesirable change in various mechanical properties. In addition, the treatment increase the porosity of the material, which may improve the rate of cellular infiltration and tissue regeneration.

For this experiment, STRATTICE™ acellular tissue matrices, as obtained from LIFECELL CORPORATION (Branchburg, N.J.) were used. STRATTICE™ is available in a pliable form and a more firm version, depending on the anatomic location from which the material was obtained. Both types were used for this experiment. The samples used for testing were cut into quarters, and three quarters were treated. Untreated samples (1 quarter) were used as controls; the controls were refrigerated during treatment. STRATTICE™ is packaged in a solution, and therefore, does not require rehydration. The treated samples were placed in 0.5 liter of cold tap water containing 55 g of MCCORMICK MEAT TENDERIZER.

Figure 2:
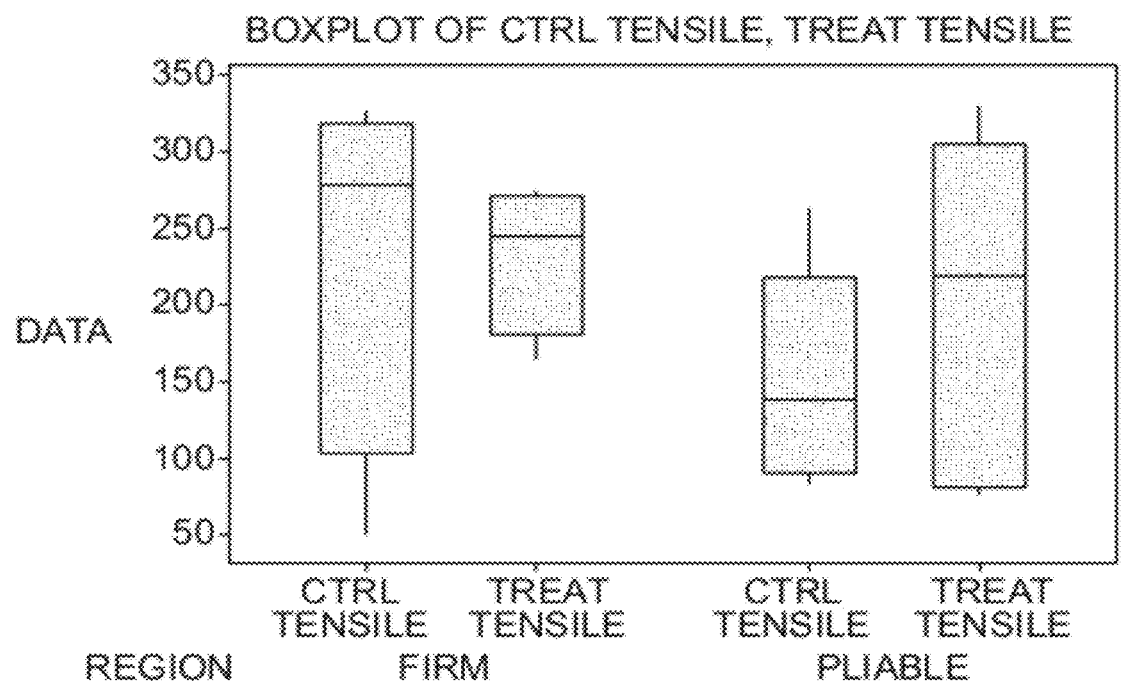
FIG. 2 is a box plot of tensile strength testing data for treated and control samples.
Figure 3:
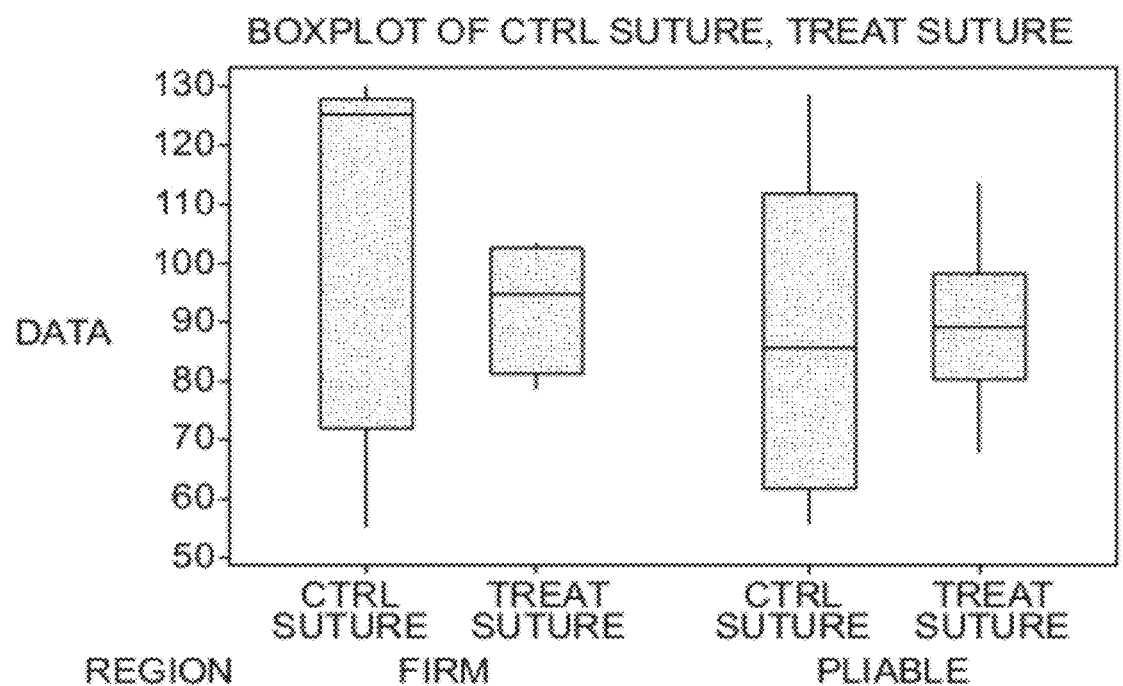
FIG. 3 is a box plot of suture strength testing data for treated and control samples.
Figure 4:
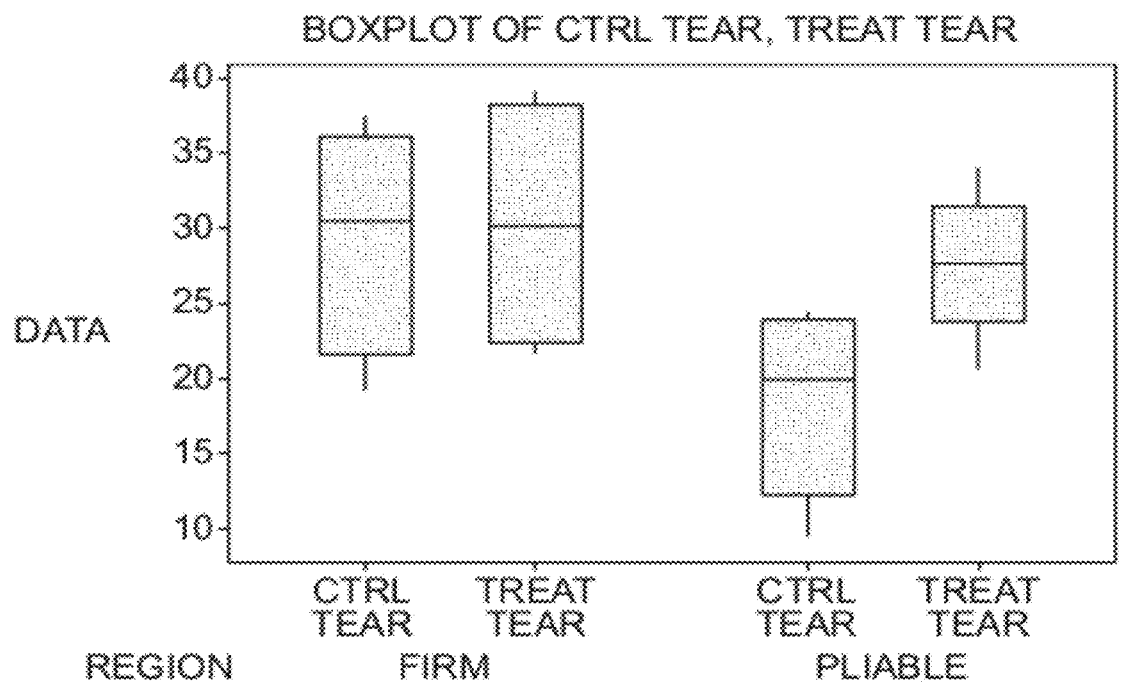
FIG. 4 is a box plot of tear strength testing data for treated and control samples.
Figure 5:
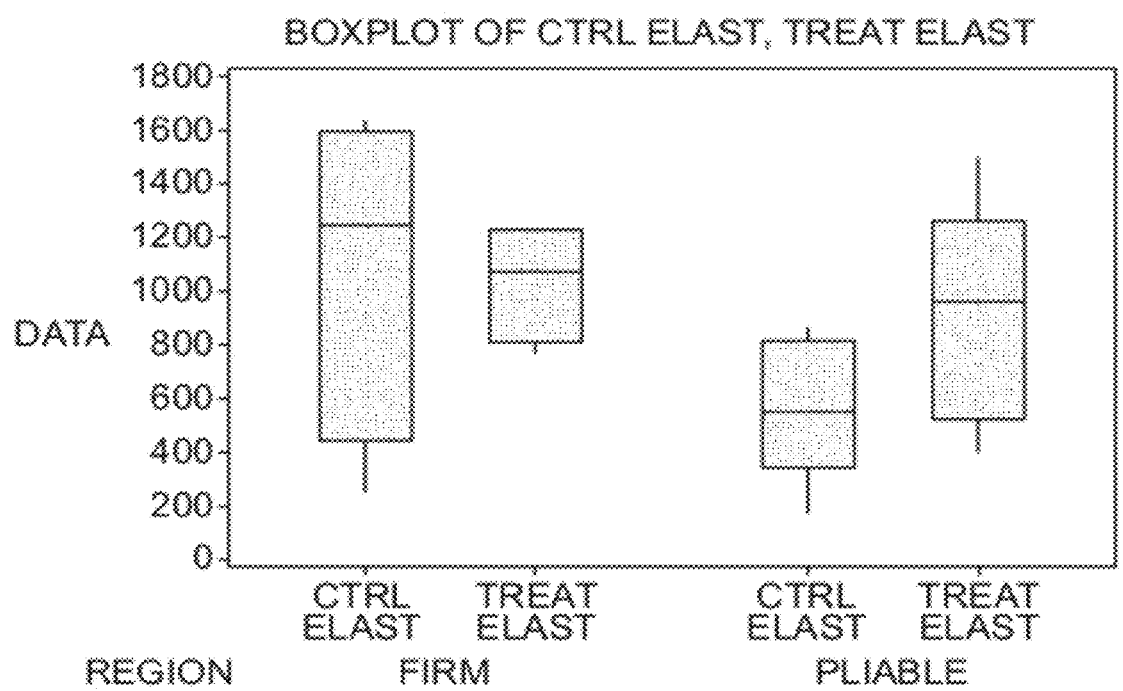
FIG. 5 is a box plot of collagenase digestion testing data for treated and control samples.
Figure 6:
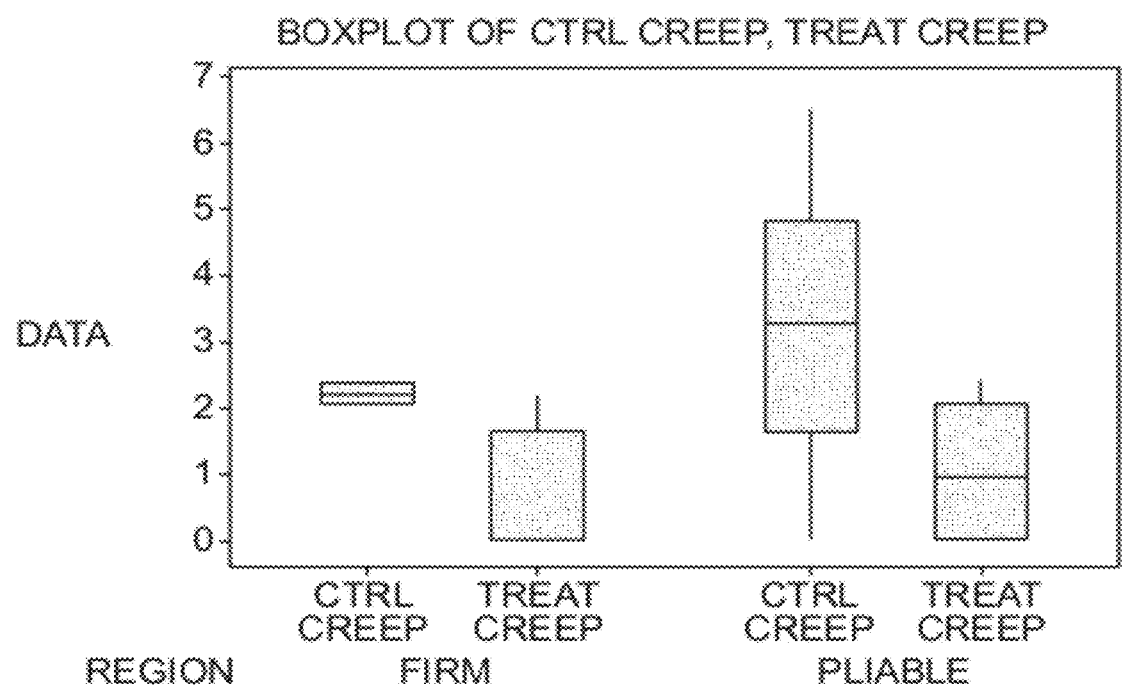
FIG. 6 is a box plot of creep resistance testing data for treated and control samples.

FIG. 1A-FIG. 1D show acellular tissue matrices after treatment with enzymes using methods of the present disclosure, as well as untreated controls. FIGS. 2-6 are box plots of tensile strengths, suture strengths, tear strengths, elastase degradation, and creep resistance for each treated and control samples. The treated samples had a noticeably increased pliability compared to controls but did not have significant reduction in other mechanical properties. In addition, no significant change in thermal transition temperature or collagenase susceptibility was found. Overall paired T-Test showed no statistical difference between control and treatment groups.

What is claimed is:

1. A method for increasing pliability in a tissue matrix, comprising:
    selecting a collagen-containing tissue matrix, and
    contacting the tissue matrix with an effective amount of proteolytic enzyme under conditions that produce an increased level of pliability in the tissue matrix;
    wherein the enzyme is at least one selected from bromelain, papain, ficin, or actinidin;
    wherein the collagen-containing tissue matrix includes a dermal tissue matrix that does not contain epidermis; and
    wherein the tissue matrix is incubated in a decellularizing solution.

2. The method of claim 1, wherein the tissue matrix is an acellular tissue matrix.

3. The method of claim 1, wherein the tissue is selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

4. The method of claim 1, wherein the enzyme is bromelain.

5. The method of claim 1, wherein the tissue matrix is contacted with the proteolytic enzyme under conditions that do not produce an undesirable change in at least one of tensile strength, tear strength, suture strength, creep resistance, burst strength, thermal transition temperature.

6. The method of claim 1, wherein the tissue matrix is contacted with the proteolytic enzyme under conditions that increase the porosity of the tissue matrix.

7. The method of claim 1, wherein the tissue matrix is contacted with the proteolytic enzyme under conditions that do not cause a statistically significant reduction in at least one of tensile strength, tear strength, suture strength, creep resistance, or thermal transition temperature.

8. A method for increasing pliability in a tissue matrix, comprising:
    selecting a collagen-containing acellular tissue matrix, and
    contacting the tissue matrix with an effective amount of proteolytic enzyme under conditions that produce an increased level of pliability in the tissue matrix;
    wherein the enzyme is at least one selected from bromelain, papain, ficin, or actinidin;
    wherein the collagen-containing tissue matrix includes a dermal tissue matrix that does not contain epidermis; and
    wherein the tissue matrix is incubated in a decellularizing solution.

9. The method of claim 8, wherein the acellular tissue matrix is selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

10. The method of claim 8, wherein the enzyme is bromelain.

11. The method of claim 8, wherein the tissue matrix is contacted with the proteolytic enzyme under conditions that do not produce an undesirable change in at least one of tensile strength, tear strength, suture strength, creep resistance, burst strength, or thermal transition temperature.

12. The method of claim 8, wherein the tissue matrix is contacted with the proteolytic enzyme under conditions that do not cause a statistically significant reduction in at least one of tensile strength, tear strength, suture strength, creep resistance, or thermal transition temperature.

* * * * *